(12) United States Patent
Reynard (10) Patent No.: US 12,274,640 B1
(45) Date of Patent: Apr. 15, 2025

(54) IMPLANT FOR ELECTROLYSIS OF AQUEOUS HUMOR

(71) Applicant: Michael Reynard, Santa Monica, CA (US)

(72) Inventor: Michael Reynard, Santa Monica, CA (US)

(*) Notice: Subject to any disclaimer, the term of this patent is extended or adjusted under 35 U.S.C. 154(b) by 0 days.

(21) Appl. No.: 18/941,644

(22) Filed: Nov. 8, 2024

(51) Int. Cl.
*A61F 9/00* (2006.01)
*A61F 9/007* (2006.01)
*A61N 1/05* (2006.01)

(52) U.S. Cl.
CPC ........ *A61F 9/0017* (2013.01); *A61F 9/00781* (2013.01); *A61N 1/05* (2013.01)

(58) Field of Classification Search
CPC .......................... A61F 9/0017; A61F 9/00781
See application file for complete search history.

(56) References Cited

U.S. PATENT DOCUMENTS

| | | |
|---|---|---|
| 3,398,069 A | 8/1968 | Juda |
| 3,399,131 A | 8/1968 | Edouard et al. |
| 3,441,488 A | 4/1969 | Onstott |
| 4,105,528 A | 8/1978 | Hasebe |
| 4,495,048 A | 1/1985 | Murakami et al. |
| 4,603,697 A | 8/1986 | Kamerling |
| 4,758,322 A | 7/1988 | Sioli |
| 4,969,986 A | 11/1990 | McIntyre et al. |
| 5,005,577 A | 4/1991 | Frenkel |
| 5,024,223 A | 6/1991 | Chow |
| 5,071,408 A | 12/1991 | Ahmed |
| 5,076,902 A | 12/1991 | Joshima et al. |
| 5,112,463 A | 5/1992 | Zhang et al. |
| D330,766 S | 11/1992 | Mann |
| 5,178,604 A | 1/1993 | Baerveldt et al. |
| 5,194,132 A | 3/1993 | Hartman et al. |
| 5,288,383 A | 2/1994 | Sparwald et al. |
| 5,558,629 A | 9/1996 | Baerveldt et al. |
| 5,725,493 A | 3/1998 | Avery et al. |
| 5,843,297 A | 12/1998 | Schmid et al. |
| 5,935,155 A | 8/1999 | Humayun et al. |
| 6,071,386 A | 6/2000 | Puthawala |

(Continued)

FOREIGN PATENT DOCUMENTS

WO    1999/016934 A1    4/1999

OTHER PUBLICATIONS

Cara Young and Leonard Seibold, "24-Hour IOOP Monitoring: Current State and Future Directions", Glaucoma Physician, Mar. 2018.

(Continued)

*Primary Examiner* — Paula J Stice
(74) *Attorney, Agent, or Firm* — Richard A. Baker, Jr.

(57) ABSTRACT

An implant and method for regulating the intraocular pressure of an eye is described. The implant is disposed in Schlemm's canal of an eye through ab-externo or ab-interno canaloplasty. Once inserted, the implant monitors the intraocular pressure of an eye with a pressure sensor and provides regulated current to electrodes within the implant to perform electrolysis. Electrolysis causes a release of gas from the eye and a reduction in the volume of aqueous humor to decrease intraocular pressure. The degree of electrolysis and reduction of intraocular pressure is regulated by a platform that includes monitoring by a pressure sensor, safety controls, and remote access.

20 Claims, 9 Drawing Sheets

(56) References Cited

U.S. PATENT DOCUMENTS

| | | |
|---|---|---|
| 6,533,768 B1 | 3/2003 | Hill |
| RE38,066 E | 4/2003 | Puthawala |
| 6,638,413 B1 | 10/2003 | Weinberg et al. |
| 6,712,764 B2 | 3/2004 | Jeffries et al. |
| 6,716,331 B2 | 4/2004 | Chikuma |
| 6,749,568 B2 | 6/2004 | Fleischman et al. |
| 6,800,206 B2 | 10/2004 | Robinson |
| 7,452,449 B2 | 11/2008 | Weinberg et al. |
| 7,638,021 B2 | 12/2009 | Blenkiron et al. |
| 7,720,549 B2 | 5/2010 | Schroeppel et al. |
| 7,828,942 B2 | 11/2010 | Cocking |
| 7,909,968 B2 | 3/2011 | Hallenbeck |
| 8,048,276 B2 | 11/2011 | Balestrino et al. |
| 8,062,500 B2 | 11/2011 | Sumita |
| 8,075,749 B2 | 12/2011 | McAlister |
| 8,123,916 B2 | 2/2012 | Blenkiron et al. |
| 8,131,375 B2 | 3/2012 | Greenberg et al. |
| 8,195,266 B2 | 6/2012 | Whalen et al. |
| 8,353,906 B2 | 1/2013 | Joshi et al. |
| 8,380,326 B2 | 2/2013 | Greenberg et al. |
| 8,419,673 B2 | 4/2013 | Rickard |
| 8,428,728 B2 | 4/2013 | Sachs |
| 8,506,515 B2 | 8/2013 | Burns et al. |
| 8,518,680 B2 | 8/2013 | Kuhry et al. |
| 8,527,055 B2 | 9/2013 | Rickard |
| 8,606,358 B2 | 12/2013 | Sachs |
| 8,608,664 B2 | 12/2013 | Kunitake et al. |
| 8,691,060 B2 | 4/2014 | Haryu et al. |
| 8,709,220 B2 | 4/2014 | Nakazawa et al. |
| 8,808,224 B2 | 8/2014 | Rickard |
| 8,894,829 B2 | 11/2014 | Haryu et al. |
| 8,918,181 B2 | 12/2014 | Ackermann et al. |
| 8,939,906 B2 | 1/2015 | Huang et al. |
| 8,961,750 B2 | 2/2015 | Zadorozhny et al. |
| 8,964,646 B2 | 2/2015 | Ohayon et al. |
| 9,011,651 B2 | 4/2015 | Greenbaum |
| 9,066,782 B2 | 6/2015 | Niksch et al. |
| 9,095,723 B2 | 8/2015 | Ackermann et al. |
| 9,125,290 B2 | 9/2015 | Greenberg et al. |
| 9,226,850 B2 | 1/2016 | Baerveldt et al. |
| 9,254,168 B2 | 2/2016 | Palanker |
| 9,268,153 B2 | 2/2016 | Blum et al. |
| 9,271,869 B2 | 3/2016 | Horvath et al. |
| 9,307,905 B2 | 4/2016 | Shen et al. |
| 9,333,115 B2 | 5/2016 | Dos Santos |
| 9,339,187 B2 | 5/2016 | Rickard |
| 9,375,348 B2 | 6/2016 | Gunn |
| 9,409,011 B2 | 8/2016 | Tai et al. |
| 9,504,606 B2 | 11/2016 | Gunn et al. |
| 9,700,721 B2 | 7/2017 | Caparso et al. |
| 10,252,048 B2 | 4/2019 | Loudin et al. |
| 10,285,856 B2 | 5/2019 | Tu et al. |
| 10,335,030 B2 | 7/2019 | Alhourani |
| 10,391,312 B2 | 8/2019 | Masko et al. |
| 10,426,958 B2 | 10/2019 | Loudin et al. |
| 10,492,948 B2 | 12/2019 | Baerveldt |
| 10,548,769 B2 | 2/2020 | Venkatraman et al. |
| 10,610,686 B2 | 4/2020 | Lee |
| 10,682,514 B2 | 6/2020 | Mowery et al. |
| 10,835,748 B2 | 11/2020 | Ackermann et al. |
| 10,987,033 B2 | 4/2021 | Martin et al. |
| 11,191,961 B2 | 12/2021 | Simon et al. |
| 11,363,951 B2* | 6/2022 | Burns ..................... A61F 9/007 |
| 11,480,813 B2 | 10/2022 | Kubota et al. |
| 11,786,168 B2 | 10/2023 | Rogers et al. |
| 12,042,432 B1* | 7/2024 | Reynard .............. A61N 1/0526 |
| 2002/0099359 A1* | 7/2002 | Santini, Jr. ............ A61F 9/0017 |
| | | 604/521 |
| 2004/0186533 A1 | 9/2004 | Greenberg et al. |
| 2007/0173905 A1 | 7/2007 | Greenberg et al. |
| 2010/0274259 A1* | 10/2010 | Yaron ................. A61M 27/002 |
| | | 604/8 |
| 2011/0022118 A1 | 1/2011 | Rickard |
| 2011/0132751 A1 | 6/2011 | Smedley |
| 2012/0130398 A1 | 5/2012 | Ackermann et al. |
| 2012/0140167 A1 | 6/2012 | Blum |
| 2015/0088156 A1 | 3/2015 | Ackermann et al. |
| 2015/0211131 A1 | 7/2015 | Jacobs |
| 2015/0335900 A1 | 11/2015 | Ackermann et al. |
| 2016/0015265 A1 | 1/2016 | Mandel et al. |
| 2017/0007834 A1 | 1/2017 | Irazoqui et al. |
| 2017/0127941 A1 | 5/2017 | Ostermeier et al. |
| 2017/0258635 A1 | 9/2017 | Reynard |
| 2019/0076296 A1* | 3/2019 | Van Meter ............ A61F 9/00781 |
| 2020/0179705 A1 | 6/2020 | Ternes et al. |
| 2020/0185951 A1 | 6/2020 | Osada |
| 2020/0188660 A1 | 6/2020 | Franke et al. |
| 2020/0330765 A1* | 10/2020 | Reynard ................ A61N 1/3603 |
| 2020/0368064 A1 | 11/2020 | Irazoqui et al. |
| 2023/0119048 A1 | 4/2023 | Irazoqui et al. |
| 2023/0181312 A1 | 6/2023 | Wortz et al. |
| 2024/0216170 A1* | 7/2024 | Lee ........................ A61F 9/0026 |

OTHER PUBLICATIONS

"Ahmed Glaucoma Valve", ad from New World Medical, Inc, purportedly from Ophthalmology Times, Feb. 15, 1999.

Rodney Grimes, "Medical Device Design", applianceDESIGN, Jun. 2017.

"Analytical Toolkit for the Optimization of Battery Electrode Materials", Malvern Panalytical, 2020.

Carl Falcon, "Improving Data Transfer and Battery Life for Implanted Devices", Medical Device and Diagnostic Industry, Jun. 2005.

John Rogers, "Electronics for the Human Body", JAMA (vol. 313:6), Feb. 10, 2015.

Enrique Spinelli and Marcelo Haberman, "Insulating electrodes: a review on biopotential front ends for dielectric skin-electrode interfaces", Physiol. Meas. 31 S183, Sep. 10, 2010 (Abstract only).

H Burkhard Dick, Ronald D Gerste, "Future Intraocular Lens Technologies", Ophthalomology, Dec. 2020 (Abstract only).

"Innovation in Glaucoma", Glaucoma Today, Winter 2010.

Sorachon Yoriya, "Effect of Inter-Electrode Spacing on Electrolyte Properties and Morphologies of Anodic $TiO_2$ Nanotube Array Films", Int. J. Electrochem. Sci., Oct. 1, 2012.

Desiree Ifft, "Keeping a Closer Watch on IOP", Glaucoma Physician, Dec. 2017.

Jeremy Lug and Randolph Sablich, "Just Make it Smaller", MDTmag.com, Jul./Aug. 2012.

Prethy Rao, Edward Wood, and Tamer Mahmoud, "Current Status of Subretinal Delivery Devices", Retinal Physician, Apr. 2023.

David Schatz, "Wireless Power for Medical Devices", Medical Device and Diagnostic Industry, Jul. 2013.

"Electrolysis of Water", Wikipedia, Mar. 13, 2016.

Mark Brinton, Jae Lim Chung, Andrea Kossler, Koung Hoon Kook, Jim Loudin, Manfred Franke, and Daniel Palanker, "Electronic enhancement of tear secretion", J Neural Eng, Feb. 2016.

Megan Brooks, "FDA Clears New Contact Lens that Senses Eye Pressure Changes", Medscape Medical News, Mar. 7, 2016.

Shiyi Liu, Xueling Meng, Jianwei Zhang, Junseok Chae, "A wireless fully-passive acquisition of biopotentials", Biosensors and Bioelectronics, Aug. 15, 2019.

Mesut Sahin and Victor Pikov, "Wireless Microstimulators for Neural Prosthetics", Crit Rev Biomed Eng., Jul. 2011.

Shiyi Liu, Ali Navaei, Xueling Meng, Mehdi Nikkhah, Junseok Chae, "Wireless Passive Stimulation of Engineered Cardiac Tissues", ACS Sens., 2017.

Orzalesi, N. et al. "Effect of Timolol, Latanaprost, and Dorzolamide on Circadian IOP in Glaucoma or Ocular Hypertension", Invest Ophthalmol Vis Sci, vol. 9, Aug. 2000, pp. 2566-2573.

Nagai, N. et al. "Existence of optimum space between electrodes on hydrogen production by water electrolysis", Int J Hyd Energy, vol. 28, 2003, pp. 35-41.

Andrew Rabinowitz, "A New Look at Glaucoma Shunts", Ophthalmology Management, Apr. 2009.

Manik Goel, Renata G. Picciani, Richard K. Lee and Sanjoy K. Bhattacharya, "Aqueous Humor Dynamics: A Review", The Open Ophthalmology Journal, 2010, 4, 52-59.

(56) References Cited

OTHER PUBLICATIONS

Parthopratim Dutta Majumder, "Anatomy of Anterior Chamber", webpage downloaded on Apr. 6, 2021 rfom www.eophtha.com/posts/anatomy-of-anterior-chamber# :~:text=Anterior chamber is an angular,a part of cilliary body.&text=Anterior chamber is 3 mm,ml of the aqueous humour.
Lance Lyons and Arthur Sit, "An Update on Implantable IOP Monitoring", Glaucoma Physician, Mar. 2021.
Anna Do and Joseph Panarelli, "Changes in Glaucoma Management Following Diurnal Home Tonometry", Glaucoma Physician, Mar. 2023.
Thierry Malvache, "Microcables Open Up New Dimensions in Invasive Surgery", MDTmag.com, Aug. 2018.
Susan Zaks, "Sensors Address Critical Healthcare Needs", MDTmag.com, Aug. 2018.
"The Ahmed Glaucoma Valve", New World Medical, Feb. 2018.
Jason Cheng, et al., "Priming the Ahmed Glaucoma Valve: Pressure Required and Effect of Overpriming", Glaucoma Journal, 0(0) 2014.
Won Kim, "Subconjunctival Glaucoma Devices", Glaucoma Physician, Jun. 2021.
Busquets, Miguel, et al., "Current State of Telemonitoring in Retina", "Retinal Physician", May 2024.
Enders, Philip, et al., "Device profile of the EYEMATE-IO™ system forintraocular pressure monitoring: overview of itssafety and efficacy", Expert Rev Med Devices, Jun. 2020;17(6):491-497.
Zhang, Wenlei, et al., "Strength and toughness of tissue adhesives depend on thickness", Giant, vol. 16, Dec. 2023.

\* cited by examiner

IMPLANT FOR ELECTROLYSIS OF AQUEOUS HUMOR

CROSS-REFERENCE TO RELATED APPLICATIONS

This is a priority patent application.

BACKGROUND

The present inventions relate to treatments for glaucoma, and more particularly, to an ocular implant for treating glaucoma.

Glaucoma is a blinding disease that is typically associated with elevation of intraocular pressure. Increased pressure in the eye can cause permanent damage to the optic nerve with loss of vision.

The eye is a complex structure made up of various tissues, including the cornea, lens, retina, and optic nerve, that work together to provide the sense of sight. The intraocular pressure in the eye is maintained by the production and drainage of aqueous humor (aqueous), a clear fluid that is produced by the ciliary body in the posterior chamber of the eye. The aqueous humor passes through the pupil and into the anterior chamber. The anterior chamber of the eye has a volume of 250 microliters. Aqueous humor then sequentially traverses through a sieve-like structure known as the trabecular meshwork and into Schlemm's canal. From Schlemm's canal, aqueous humor drains into collector channels. Aqueous humor normally drains from the anterior chamber through the trabecular meshwork of the eye and into outflow collector channels at a rate of 2 to 3 microliters per minute. Dysfunction in the pathway of aqueous humor drainage can result in elevated intraocular pressure, optic nerve damage, and progressive loss of vision.

Glaucoma is commonly caused by impaired drainage of aqueous humor at the level of the trabecular meshwork or outflow collector channels.

The effectiveness of pharmacologic treatment is limited by physiologic variations of intraocular pressure. Diurnal variation is the most notable example of physiologic fluctuation of intraocular pressure. The diurnal variation of intraocular pressure in normal subjects during daytime hours varies between 3-6 mm Hg. In patients with glaucoma, the 24-hour variation of intraocular pressure can be as much as 18 mm Hg. The pressure-lowering effect of medications applied during the day dissipates towards the end of the day and may not be present during nocturnal hours when intraocular pressure may be at its highest level.

Pharmacologic treatment for glaucoma is expensive and not available to many people who have limited income or who live in remote areas. Medications for glaucoma have significant risks for complications. Many patients with glaucoma require multiple forms of therapy to control their condition.

The present inventions provide a method and device for changing aqueous humor into gasses that dissipate into the atmosphere, thereby reducing the volume of aqueous humor in the eye and lowering the pressure in the eye.

BRIEF SUMMARY

In some aspects, the techniques described herein relate to an apparatus including an ocular implant with a curved longitudinal central axis with a bend in a curvature plane, the ocular implant including a central channel and an array of perforations along walls of the ocular implant, configured to be disposed within Schlemm's canal of an eye; a pair of electrodes lining an inside of the walls of the ocular implant; a controller electrically connected to the pair of the electrodes; and a power source within the ocular implant electrically connected to the controller.

In some aspects, the techniques described herein relate to an apparatus wherein the power source delivers electrical current to the electrodes.

In some aspects, the techniques described herein relate to an apparatus wherein the electrodes are arranged in a coil within the ocular implant.

In some aspects, the techniques described herein relate to an apparatus further including a pressure sensor electrically connecting to the controller, the pressure sensor configured to detect pressure within the ocular implant.

In some aspects, the techniques described herein relate to an apparatus further including an antenna electrically connected to the controller, said antenna configured to wirelessly communicate with a remote receiver.

In some aspects, the techniques described herein relate to an apparatus where the electrodes are made of stainless steel.

In some aspects, the techniques described herein relate to an apparatus where the ocular implant is made of polyurethane.

In some aspects, the techniques described herein relate to an apparatus further including a lumen at an end of the ocular implant, the lumen configured to receive aqueous humor from the eye.

In some aspects, the techniques described herein relate to a method including performing a fornix-based conjunctival peritomy; creating a scleral flap beneath a conjunctiva in a region of the fornix-based conjunctival peritomy; exposing Schlemm's canal; inserting a proximal end of the ocular implant into an incision into the Schlemm's canal, where the ocular implant includes a central channel and an array of perforations along walls of the implant, a pair of electrodes lining an inside of the walls of the ocular implant, a controller electrically connected to the pair of the electrodes, and a power source within the ocular implant electrically connected to the controller; suturing the scleral flap; and signaling the controller to perform electrolysis by energizing the electrodes.

In some aspects, the techniques described herein relate to a method where the signal determines that current is delivered by the power source to the electrodes.

In some aspects, the techniques described herein relate to a method where the signal from the controller to perform electrolysis regulates a level of current, a duration of the current, and a timing of the current.

In some aspects, the techniques described herein relate to a method where the perforations in the walls allow ingress of aqueous humor into the central channel of the ocular implant.

In some aspects, the techniques described herein relate to a method where the perforations in the walls allow egress of gas from the central channel of the ocular implant.

In some aspects, the techniques described herein relate to a method where the electrodes are made of aluminum.

In some aspects, the techniques described herein relate to a method where the electrodes are made of a polymer metal combination.

In some aspects, the techniques described herein relate to a method including: receiving a signal from a remote device at a controller in a ocular implant, where the ocular implant is located in Schlemm's canal of an eye, where the ocular implant includes a central channel and an array of perforations along walls of the ocular implant, a pair of electrodes lining an inside of the walls of the ocular implant, the controller electrically connected to the pair of the electrodes, a pressure sensor electrically connecting to the controller, and a power source within the ocular implant electrically connected to the controller; detecting a pressure within the ocular implant with the pressure sensor; analyzing the pressure with the controller and determining if electrolysis is required to reduce the pressure; energizing the electrodes based on a signal from the controller; monitoring the pressure with the pressure sensor until the pressure indicates that electrolysis needs to be subdued or no longer required; and reducing the energy to the electrodes based on the signal from the controller.

In some aspects, the techniques described herein relate to a method where the signal determines that current is delivered by the power source to the electrodes.

In some aspects, the techniques described herein relate to a method where the perforations in the walls allow ingress of aqueous humor into the central channel of the ocular implant.

In some aspects, the techniques described herein relate to a method where the perforations in the walls allow egress of gas from the central channel of the ocular implant.

In some aspects, the techniques described herein relate to a method where the ocular implant is made of silicone.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

All illustrations of the drawings are for the purpose of describing selected versions of the present invention and are not intended to limit the scope of the present invention.

The present document relates to an ocular implant 202 directed to the treatment of glaucoma. The described technique includes the insertion of a flexible tube-like implant 202 into Schlemm's canal 112 by utilizing an ab-externo and ab-interno canaloplasty. The implant 202 has a power supply and regulator that provides controlled electrical current to electrodes. Conversion of aqueous humor 124 to gas occurs when it is in contact with adequately charged electrodes. The implant 202 is designed to be disposed within Schlemm's canal 112 of an eye 100.

Described here is a method and implant 202 for decreasing the amount of aqueous humor 124 in the eye 100 to reduce intraocular pressure. The implant 202 consists of a flexible fenestrated implant that resides in Schlemm's canal 112. The implant 202 has an inner cylindrical wall that is lined by opposing electrodes. A source of power within the implant 202 delivers current to the aqueous humor 124 within the lumen 210 of the implant 202. Aqueous humor 124 converted into gas by means of electrolysis escapes through fenestrations in the implant 202 and passes into collector channels and into the venous plexus system where it either dissolves or is dissipated through the outer wall of the eye 100.

Figure 1:
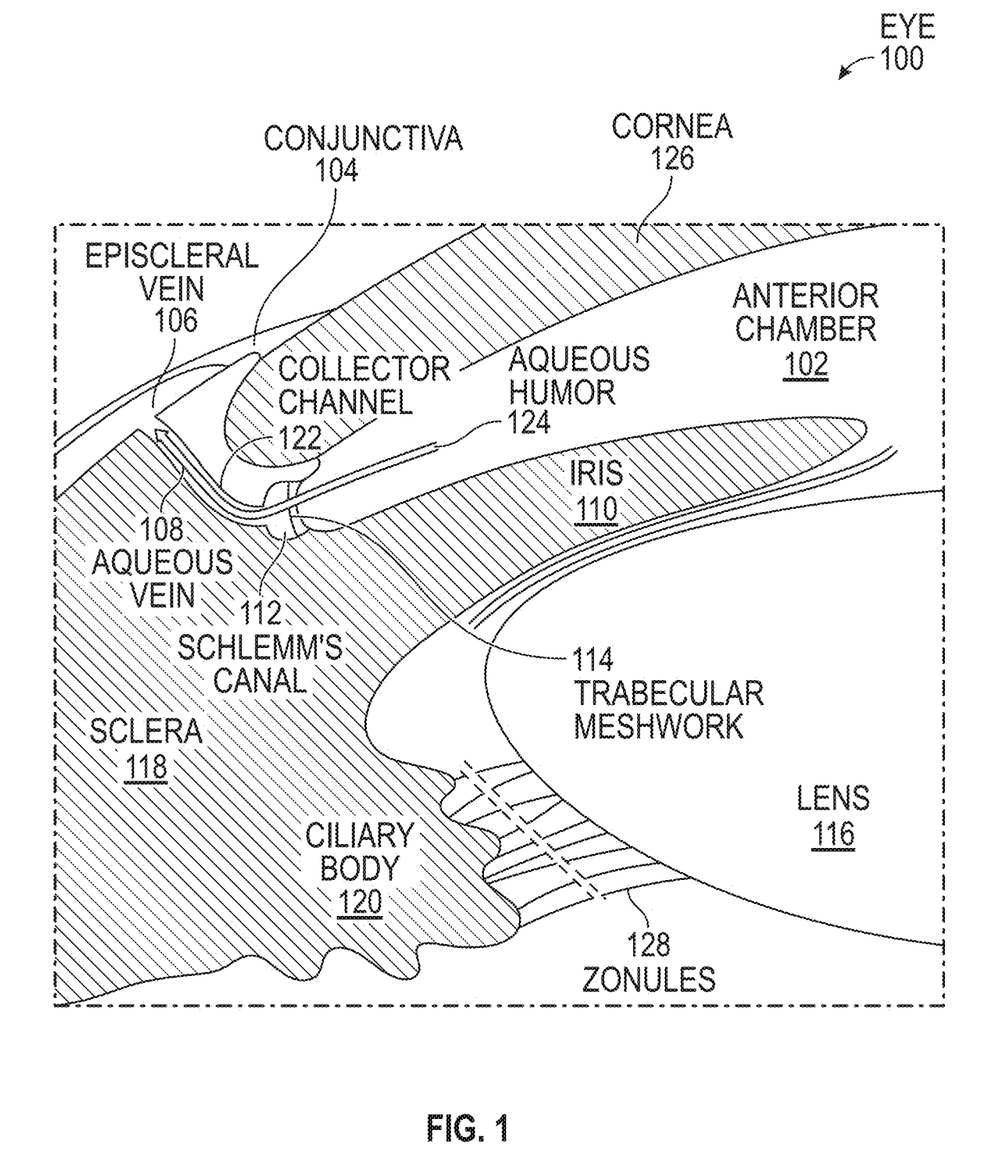
FIG. 1 shows a stylized, cross-sectional view of the eye and several structures involved in the flow of aqueous humor.

FIG. 1 is a diagram of the surface of the eye 100 that is relevant to the pressure within the eye 100. The cornea 126 forms the anterior portion of the eye 100. The cornea 126 consists of transparent tissue composed of collagen. The cornea 126 demarcates the front boundary of the anterior chamber 102. The remaining outer wall of the eye 100 is the sclera 118. The sclera 118 is covered by the conjunctiva 104. The iris 110 is the colored portion of the eye 100 that is visible through the cornea 126. The center of the iris 110 has a round aperture known as the pupil 302. Light travels through the pupil 302 and enters the lens 116. The iris 110 forms the posterior boundary of the anterior chamber 102. Behind the iris 110 is the posterior chamber. The aqueous humor 124 is located between the cornea 126 and the lens 116, and in the posterior chamber. Between the base of the iris 110 and cornea 126 is the trabecular meshwork 114. The ciliary body 120 is adjacent to the posterior chamber and the zonules 128. The trabecular meshwork 114 is connected to Schlemm's canal 112, the Collector channels 122, and the aqueous vein 108. The aqueous vein 108 is connected to the episcleral vein 106.

Aqueous Humor Fluid Dynamics

The aqueous humor 124, which is a clear fluid in the eye 100, flows through Schlemm's canal 112 as part of the eye's drainage system. The average rate of aqueous humor 124 outflow through Schlemm's canal 112 is about 2.5 microliters per minute. This outflow helps maintain the intraocular pressure within the eye 100, which is crucial for its proper function. On a daily basis, the total amount of aqueous humor 124 produced and drained is about 2.4 to 3.6 milliliters.

The aqueous humor 124 flows from Schlemm's canal 112 into the collector channels 122. The collector channels 122 are connected to the episcleral vein 106. This network of veins then transports the aqueous humor 124 into the systemic venous circulation. This is the major pathway for aqueous humor 124 drainage and is responsible for the majority of outflow from the anterior chamber 102 of the eye 100.

The conversion of aqueous humor 124 from liquid to gas, such as through evaporation, is typically negligible under normal physiological conditions. Aqueous humor 124 is contained within the eye 100 and does not normally undergo a phase change from liquid to gas in any significant quantity. The eye 100 maintains the aqueous humor 124 in a liquid state to help regulate intraocular pressure and provide nutrients to eye tissues. A change in the aqueous humor 124 from a liquid to a gas that is released from the eye 100 in a controlled manner would reduce the volume of aqueous humor in the eye and decrease intraocular pressure.

Electrolytic Conversion of Aqueous Humor

The first documented observation of electrolysis in 1800 by William Nicholson and Anthony Carlisle was reported in "A Journal of Natural Philosophy, Chemistry, and the Arts" where they reported that when a voltaic pile was connected to electrodes immersed in water, hydrogen gas evolved at the cathode, and oxygen gas evolved at the anode, effectively decomposing water into its constituent gases.

In 1834, Michael Faraday formulated two fundamental laws of electrochemical reactions. These laws form the basis of electrolysis of aqueous humor as described in this document. The first law describes the quantitative relationship between the amount of electrical charge passing through an electrolyte or fluid, and the amount of gas liberated as a result of an electrochemical reaction. Faraday's second law describes the need for ions dissolved in the fluid that is needed for electrolysis to occur. The amount of current needed for electrolysis is dependent on the capacity of the power source and the conductivity of the fluid. In the discussion herein the conductivity of aqueous humor is slightly less but still comparable with that of saline.

To determine the amount of electrical current needed to convert aqueous humor 124 to gas via electrolysis, we can refer to Faraday's laws of electrolysis. The key factors are the composition of the aqueous humor 124 (primarily water and electrolytes), and the specific chemical reactions involved in the electrolysis process.

Biochemical Calculations

The electrical current needed to achieve electrolysis is dependent on the duration over which electric current is applied, the total electric charge, electric current, and Faraday's constant (96,485 Coulombs per mole). Based on these parameters, electrolysis of 1 microliter of aqueous humor 124 would require a minimum current of approximately 0.37 milliamperes (mA).

The aqueous humor 124 flows through Schlemm's canal 112 as part of the eye's drainage system. The average rate of aqueous humor 124 outflow through Schlemm's canal 112 is about 2.5 microliters per minute, or approximately 3.6 milliliters of aqueous humor 124 each day.

Approximately 178 milliamperes (mA) of electrical current would be needed to electrolyze 1 microliter of aqueous humor 124 in one minute or 1,436 microliters in a 24-hour period of time. By comparison, a reasonable estimate is that a one-time application of 0.5% Timolol eye drops suppresses aqueous humor 124 production by approximately 0.75 microliters in one minute or 1080 microliters over a 24-hour period, assuming an average reduction rate of 30%.

Delivery of Implant for Electrolysis of Aqueous Humor

The implant 202 is an apparatus that is delivered into Schlemm's canal 112 utilizing either an approach from the outer surface of the eye 100 (ab-externo) or by means of a corneal and limbal incision (ab interno). The implant 202 contains paired electrodes that deliver current to aqueous humor 124 in the lumen 210 of the implant 202.

Figure 2:
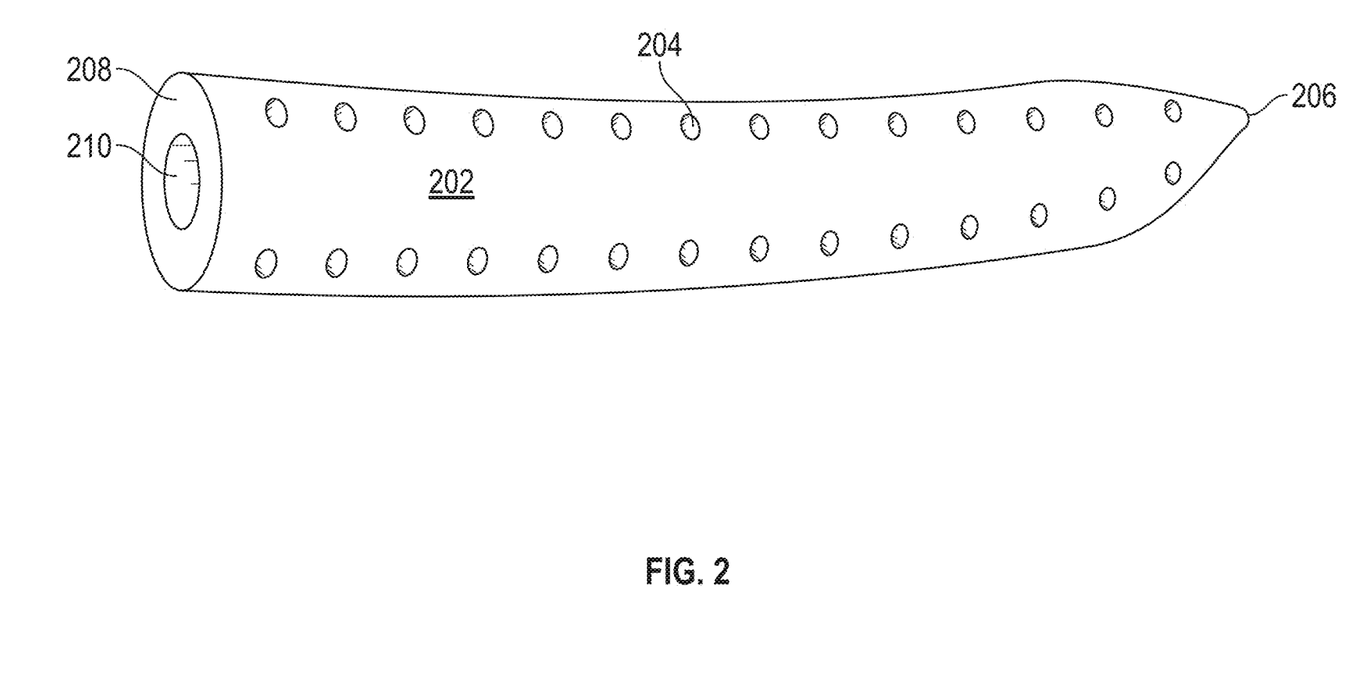
FIG. 2 shows a perspective view of the implant for delivery into Schlemm's canal.

FIG. 2 shows the implant 202 apparatus with a circumferential length of approximately 32 to 36 mm, depending on application in children or adults. The implant 202 is applied by a procedure known as canaloplasty with the proximal tip 206 of the implant 202 having a pointed tip for navigating Schlemm's canal 112 and disrupting adhesions or obstructions within the canal. The implant 202 is made from any suitable material with sufficient rigidity to allow it to be advanced through Schlemm's canal 112 and flexibility to bend and circumnavigate the canal with minimal disruption. Exemplary polymers that may be used in the implant 202 include without limitation, polyethylene, polyurethane, silicone, polytetrafluoroethylene, polyvinyl chloride, polycarbonate, polyimide, polyamide, polysulfone, polyether block amide, and fluoropolymers. A lubricant polymer or viscoelastic may be used to coat ocular tissue and the implant 202 during the procedure to enhance non-frictional placement within Schlemm's canal 112. The implant 202 may have a curved longitudinal central axis with a bend in a curvature plane, the implant 202 may include a central channel and an array of perforations 204 along the walls of the implant 202.

The wall of the implant 202 has multiple fenestrations, or perforations 204, that allow aqueous humor 124 to penetrate within the lumen 210 of the implant 202. As electrolysis is performed, aqueous humor 124 is allowed to ingress into the central channel of the implant 202, and the gas byproduct of the electrolysis is allowed to egress from the central channel of the implant 202. The lumen 210 is accessible via the distal end 208 of the implant 202. The perforations 204 do not interfere with the longitudinal placement of electrodes placed longitudinally along the inner wall of the implant 202. The electrode system is paired and located on opposite sides of the inner wall of the implant 202. Each electrode extends substantially along the inner length of the implant 202 and is between 10 microns to 250 microns in width. Alternatively, paired electrodes can be arranged as a coil that is freestanding or attached to the inner wall of the implant 202 (see FIG. 7). The electrodes can be secured to the implant 202 by being partially embedded to its inner wall or by attachment to the inner wall with biocompatible adhesives. Examples of suitable adhesives include cyanoacrylate, epoxy resin, UV-curable adhesive, silicone-based adhesive, and acrylic adhesive.

Ab-Externo Canaloplasty with Implant Insertion

Figure 3:
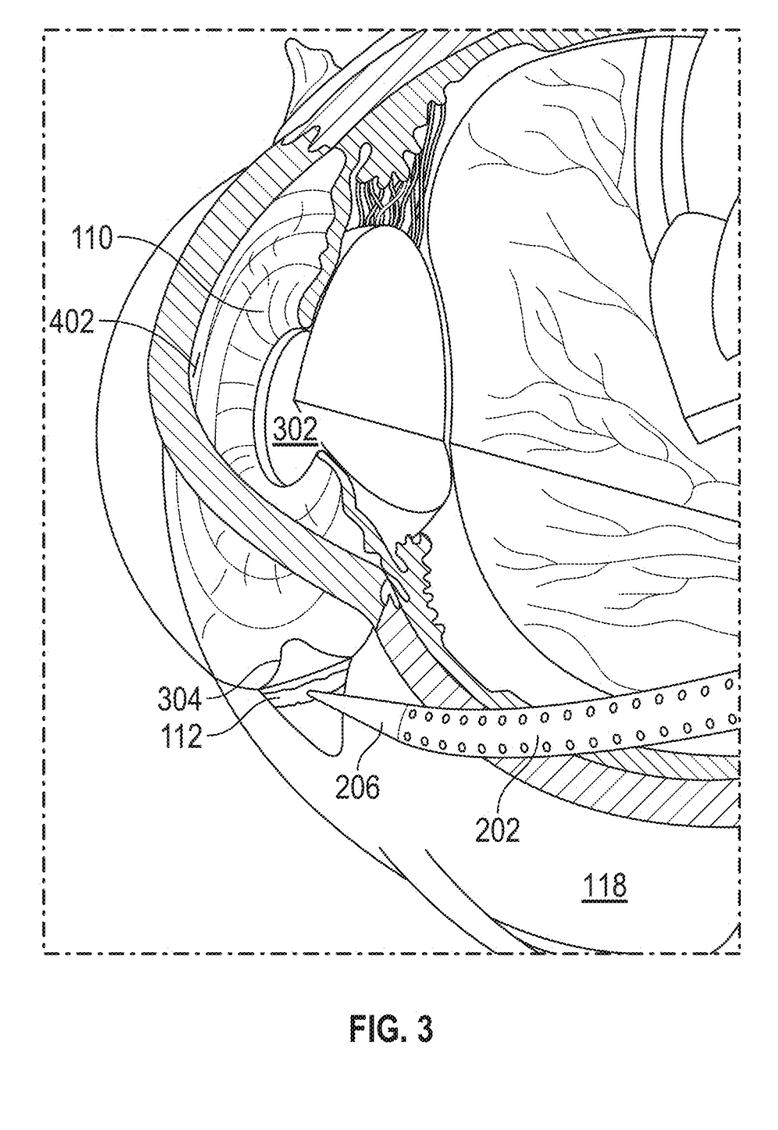
FIG. 3 shows a perspective, cut-away view of an eye with the delivery of the implant into Schlemm's canal by means of an ab-externo canaloplasty.

The implant 202 can be delivered into Schlemm's canal 112, as seen in FIG. 3, through the following steps:
1. A fornix-based conjunctival peritomy is performed.
2. A scleral flap 304 is performed beneath the conjunctiva 104 in the region of the conjunctival peritomy.
3. Dissection towards clear cornea 126 exposes Schlemm's canal 112. This provides access for creating a Goniotomy 402. The Goniotomy 402 is a short incision through the trabecular meshwork 114.
4. The proximal tip 206 of the implant is inserted through an incision into Schlemm's canal 112.
5. The implant 202 is advanced through the circumference of Schlemm's canal 112.
6. The distal end 208 of the implant 202 terminates approximately 1-2 mm short of the incision into Schlemm's canal 112.
7. The distal end 208 of the implant 202 is crimped and closed with a 10-0 nylon suture.
8. The scleral flap 304 is closed with 10-0 nylon suture and the conjunctiva 104 is also sutured in position or drawn across the area of the scleral flap.

Figure 4:
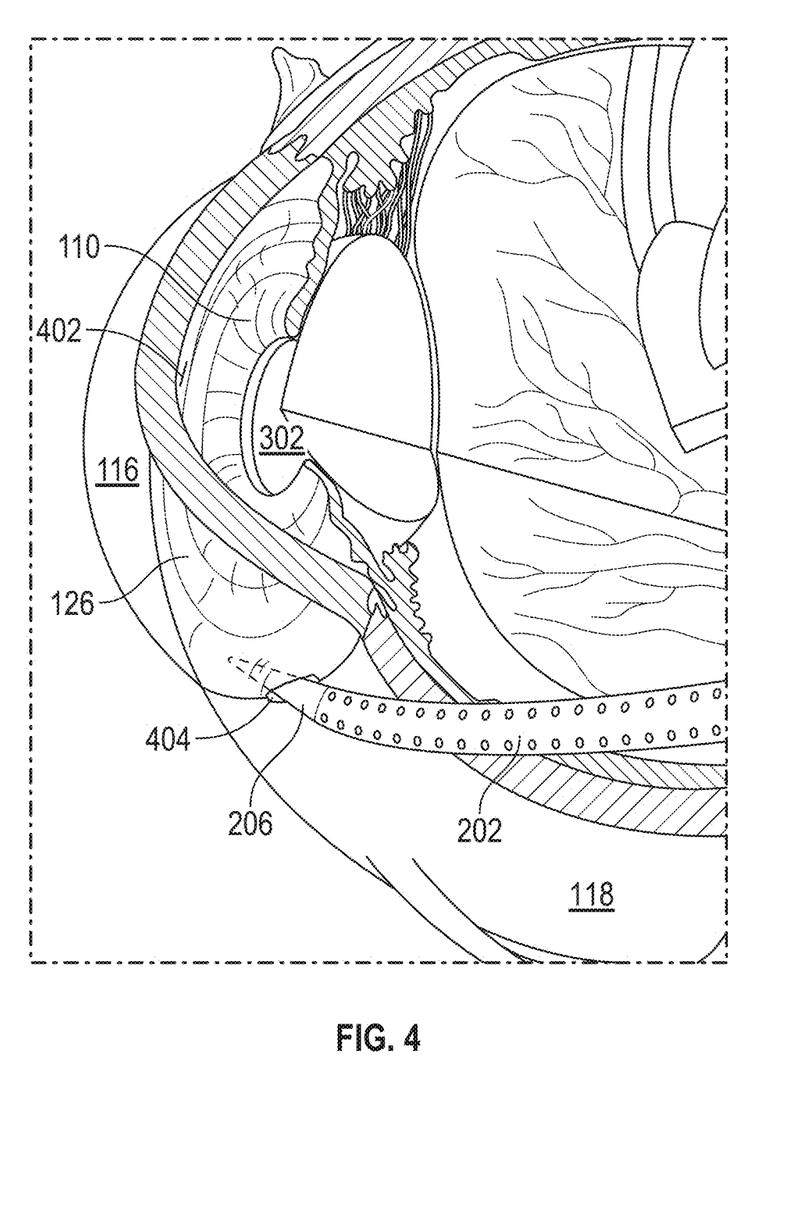
FIG. 4 shows a perspective, cut-away view of an eye with the delivery of the implant into Schlemm's canal by means of an ab-interno canaloplasty.

Note that the implant 202 in FIGS. 3 and 4 is not proportional to the drawing of the eye 100 but is drawn to illustrate the steps for insertion.

Ab-Interno Implant Insertion

The implant 202 can also be delivered into Schlemm's canal 112, as seen in FIG. 4, using an approach that does not disturb the sclera 118 and conjunctiva 104 through the following steps:
1. A limbal or clear corneal incision 404 provides access for creating a Goniotomy 402. The Goniotomy 402 is a short incision through the trabecular meshwork 114.

2. The proximal tip 206 of the implant 202 is threaded through the goniotomy using forceps or a commercially available inserter.
3. The implant 202 is threaded into Schlemm's canal 112 around the iris 110 for up to 360 degrees.
4. The distal end 208 of the implant 202 appearing in the goniotomy incision may be crimped to securely close the end of the implant 202.
5. The incisions are closed.

Figure 5:
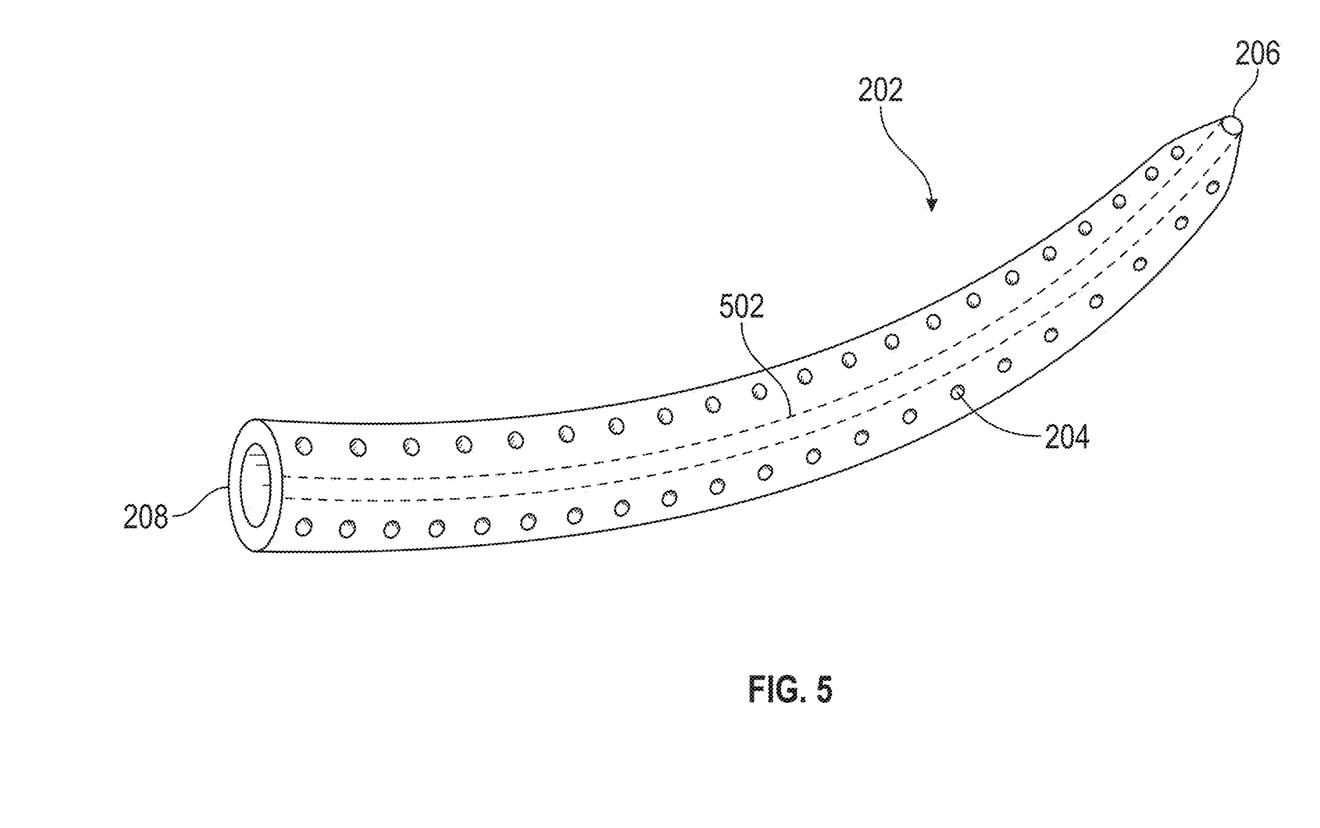
FIG. 5 depicts a sagittal view of the implant with a lining of paired electrodes.

FIG. 5 shows another view of the implant 202. The electrodes 502 are shown running the length of the inside of the implant 202. The implant 202 has perforations 204 on the sides for the length of the implant 202. The perforations 204 could be placed in any pattern and size on the walls of the implant 202, provided that the perforations 204 permit the aqueous humor 124 to reach the electrodes 502 to permit electrolysis.

The implant 202 may have an outer diameter between 150 microns to about 750 microns to accommodate the wide range of diameters found in Schlemm's canal 112. The implant 202 may also be formed to have suitable internal dimensional profiles. Exemplary profiles without limitation include circular, elliptical, square, or rectangular.

Figure 6:
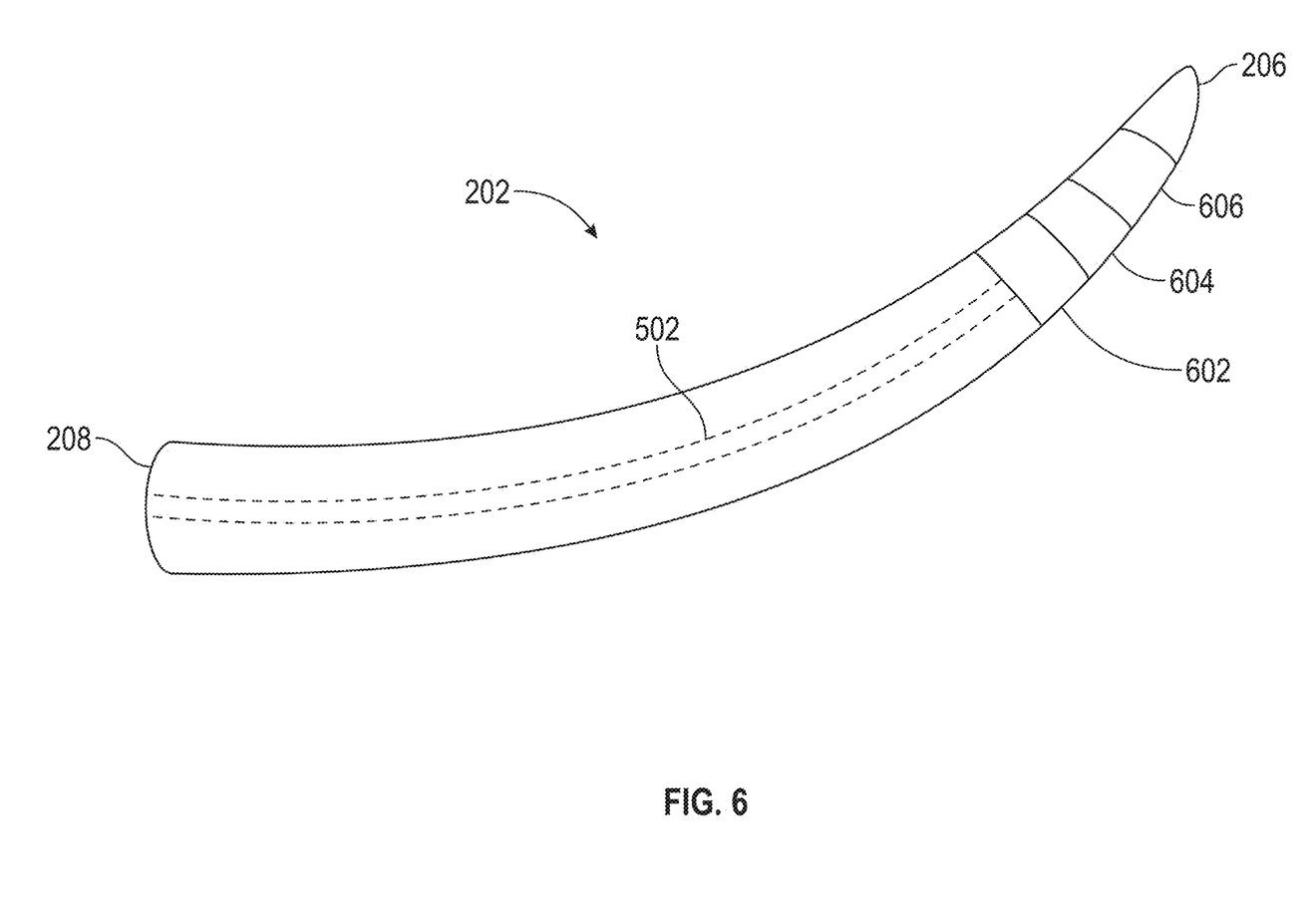
FIG. 6 shows an integrated power source, regulator, and pressure sensor within the lumen of the implant.

FIG. 6 is a cross-section of the implant 202, showing one embodiment of the physical placement of the components. The proximal tip 206 could hold a power source 606, or the power source 606 could be behind a tip designed to facilitate threading the implant 202 through Schlemm's canal 112. Next to the power source 606 could be a controller 604, followed by the pressure sensor 602. The pressure sensor 602 may detect the intraocular pressure of the aqueous humor 124 that flows into the 202 through the perforations 204. A regulator 802 could follow the pressure sensor 602, the regulator 802 powering the electrodes 502.

The proximal tip 206 of the implant 202 contains a power source 606 such as a thin-film lithium micro-battery, solid-state lithium micro battery, miniature lithium-ion battery, coil, or micro-supercapacitor. The power source 606 may be integrated with electrodes 502 that line the internal wall of the implant 202 and a pressure sensor 602 within the lumen 210 of the implant 202. The current delivered to the electrodes 502 and the pressure sensor 602 could be regulated by a controller 604 contained within the body of the implant 202. The pressure sensor 602 is electrically coupled to the controller 604 and a transponder for converting the sensor signal to a remote receiver.

Figure 7:
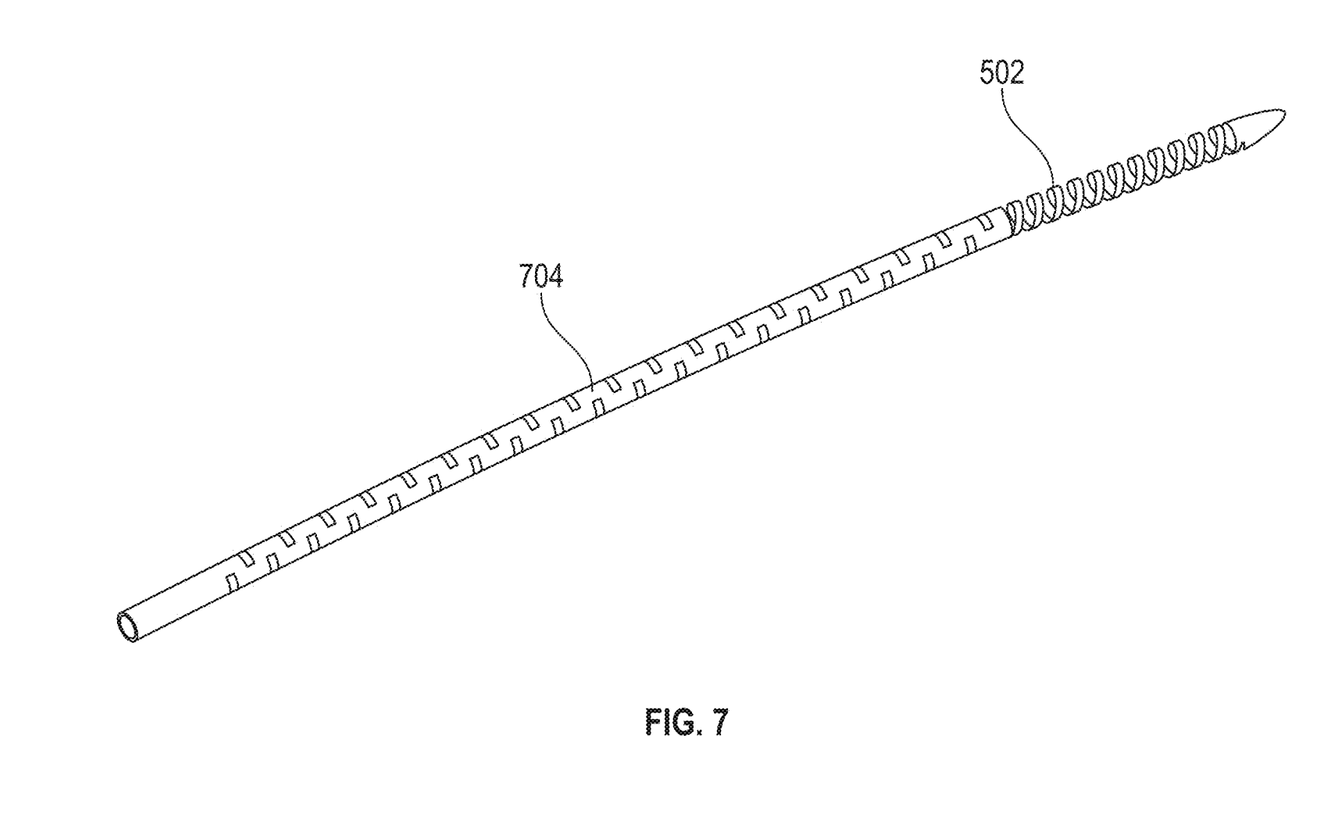
FIG. 7 illustrates an alternative embodiment with the spiral pair of electrodes from within the implant.

FIG. 7 shows an alternative embodiment of the electrodes 502.

Electrodes 502 could be a parallel coil of wires that pass electricity through the aqueous humor 124, causing the electrolysis. In some embodiments, the gas from the electrolysis passes through the ports 704, then through the perforations 204, and into the collector channels and aqueous veins.

Electrodes 502 lining the internal wall of the implant are immersed with aqueous humor 124 that enters directly into the lumen 210 of the implant. Aqueous humor 124 can also flow through the perforations of the implant wall and pass into the lumen of the implant (202). Current delivered to the electrodes 502 results in electrolysis with conversion of aqueous humor 124 into gas. The pressure gradient between the aqueous humor 124 in the lumen 210 of the implant 202 and collector channels facilitates the exit of gas through the perforations of the implant 202 walls into collector channels and aqueous veins.

The electrodes 502 that line the inner walls of the implant 202 may be selected from a multiplicity of materials that includes platinum (Pt), graphite (Carbon), stainless steel, titanium (Ti), nickel (Ni), gold (Au), palladium (Pd), silver (Ag), Nitinol®, aluminum (Al), graphene, platinum gray, and polymer-based products such as polypyrrole, polystyrene sulfonate, Poly 3,4-ethylenedioxythiophene (PEDOT), and polymer metal combinations. The preparation of platinum gray as an electrode has been described in U.S. Pat. No. 6,794,533, incorporated herein by reference in its entirety, and its utility as a miniature biocompatible electrode exemplified in U.S. Pat. No. 2014/0222103, incorporated herein by reference in its entirety.

Figure 8:
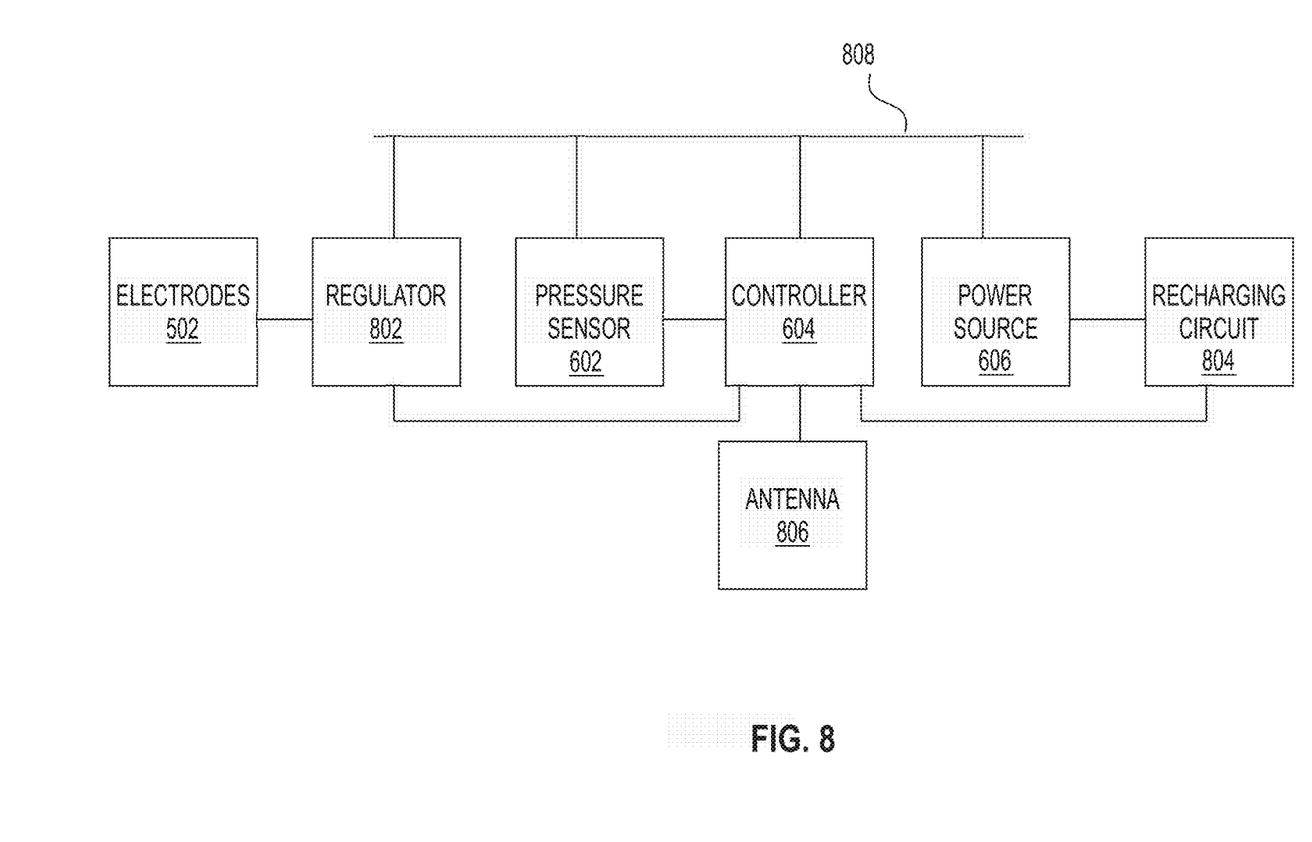
FIG. 8 illustrates one electrical embodiment of the implant.

FIG. 8 is an electrical diagram of one embodiment of the implant 202. The controller 604 could be a BLE System on a Chip such as a Cypress C4BT-423028-02. The Cypress BLE Chip includes an ARM microprocessor, and Bluetooth low energy module (which includes a transceiver) for communications via the Bluetooth protocol with a cell phone, computer, or other Bluetooth devices, 1024 KB Flash RAM, 512 KB SRAM, and numerous input and output pins for interfacing with other devices, such as antenna 806, power source 606, pressure sensor 602, regulator 802, and recharging circuit 804. The controller 604 may contain features that allow the controller 604 to go into a sleep mode until woken by a timer or with the reception of a Bluetooth message. This may allow the implant 202 to go to sleep for periods of time, perhaps minutes, hours, or days, and then wake up to check the pressure in the eye 100. In some embodiments, this period for sleeping is configurable through the Bluetooth connection. The implant 202 could also be woken up through Bluetooth communication.

In the FIG. 8 embodiment, the controller 604 is electrically connected to the power source 606 through a power rail 808, receiving power from the power rail 808 and perhaps sensing the remaining power in the power rail 808. The controller 604 may also control wireless recharging by sending signals and receiving signals from the recharging circuit 804.

The controller 604 may be connected to antenna 806 for sending signals to a computer or to a smartphone. In some embodiments, the communications is using the Bluetooth protocol. Other embodiments may use WiFi (IEEE 802.11). Still other embodiments may use cellular communications (commonly known as 3G, 4G, and/or 5G). Other standard or proprietary protocols could also be used.

The controller 604 could be electrically connected to the pressure sensor 602. In one embodiment, the controller 604 passes power to the pressure sensor 602. In other embodiments, the pressure sensor 602 is electrically connected to and receives power directly from power source 606. In some embodiments, the pressure sensor 602 both sends and receives signals from the controller 604. The signals may include current pressure readings and pressure sensor 602 configuration settings. In some embodiments, the pressure sensor 602 is connected to the power rail 808, and in other embodiments, it derives its power through the controller 604.

The controller 604 may also control, and may be electrically connected to, the electrodes 502. In some embodiments, the controller 604 will directly power the electrodes 502. Some controllers 604 have analog ports with sufficient power to create electrolysis directly from the chip. In other embodiments, a regulator 802 is used to regulate the power to the electrodes 502. In this case, the controller 604 is electrically connected to the electrodes 502 through the regulator 802. The regulator 802 in this embodiment electrically connects to the power source 606 (possibly through the power rail 808) to receive power and is electrically connected to the controller 604 to receive signals indicating the power characteristics to be sent to the electrodes 502. These characteristics may include voltage, current, frequency, and duration of discharge.

Figure 9:
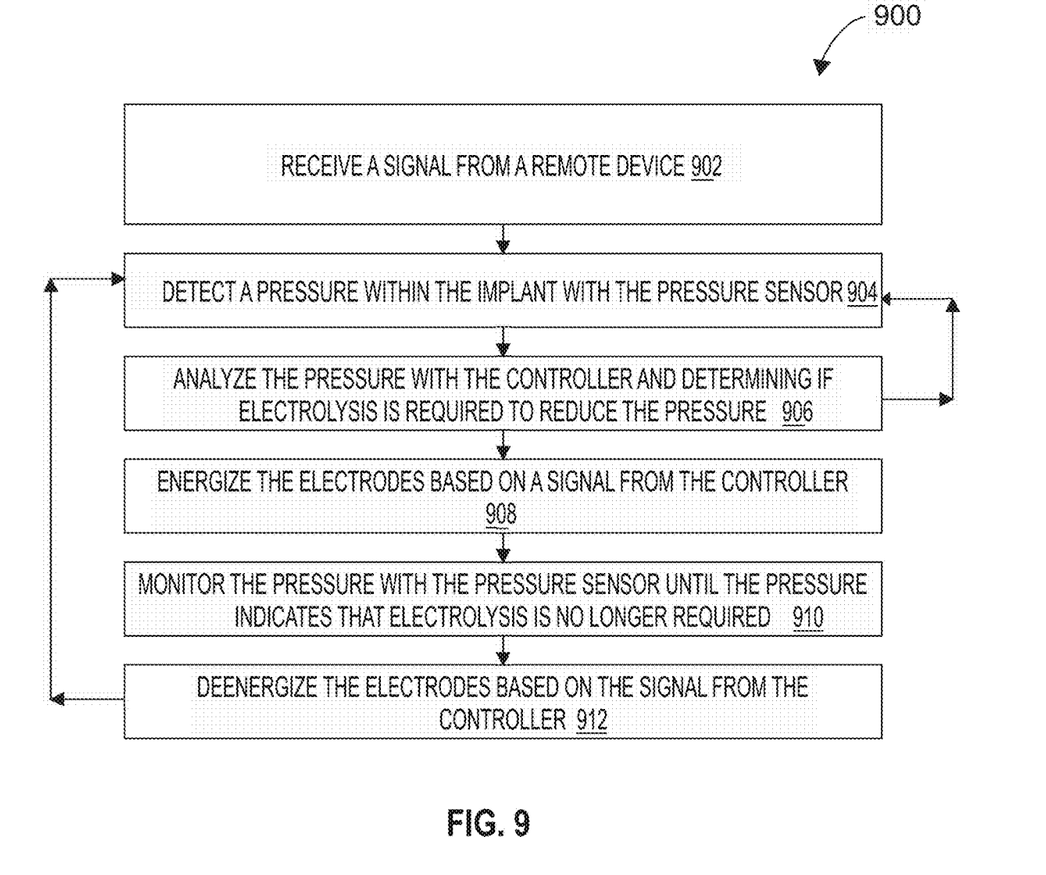
FIG. 9 illustrates the steps in an electrolysis method 900 in one embodiment.

The electrolysis method 900 in FIG. 9 is the operating instructions set for the operation of the implant 202 as it performs electrolysis in the eye 100. In block 902, the electrolysis method 900 receives a signal from a remote device at the controller 604 in the implant 202 to start the electrolysis method 900.

In block 904, the electrolysis method 900 detects the pressure of the aqueous humor 124 within the eye 100 (and thus within the implant 202) with the pressure sensor 602. The pressure sensor 602 communicates the pressure to the controller 604, either through an analog signal that an analog-digital converter (ADC) transforms into a digital value. The ADC could be in the pressure sensor 602, the controller 604, or a stand-alone device.

In block 906, the electrolysis method 900 analyzes the pressure with the controller 604 and determines if electrolysis is required to reduce the pressure by comparing the pressure to a threshold. If electrolysis is not needed, loop back to block 904. Otherwise, continue to block 908.

In block 908, the electrolysis method 900 energizes the electrodes 502 based on a signal from the controller 604. The signal could be power directly set on a pin of the controller 604. In other embodiments, a pin on the controller 604 triggers a relay to place power from power rail 808 into the electrodes 502. In still other embodiments, the controller pin signals a regulator 802 to provide power to the electrodes 502. In still another embodiment, the controller 604 provides an analog value powering the electrodes 502. In some embodiments, the controller 604 regulates the level of current sent to the electrodes 502. In some embodiments, the controller 604 regulates the duration of the current sent to the electrodes 502. In some embodiments, the controller 604 regulates the timing of the current sent to the electrodes 502.

In block 910, the electrolysis method 900 monitors the pressure with the pressure sensor 602 until the pressure indicates that electrolysis is no longer required. The monitoring requires frequent sampling of the pressure and transmitting the pressure value back to the controller 604. The controller 604 compares the pressure reading to either a fixed threshold value or to a threshold value received from the remote device.

In block 912, when the pressure is below the threshold, the controller 604 de-energizes the electrodes 502 by resetting the signal. The electrolysis method 900 then returns to block 904 to wait until the pressure sensor 602 and controller 604 determine that the pressure is above the threshold.

It is to be understood that the configurations and/or approaches described herein are exemplary in nature, and that these specific embodiments or examples are not to be considered in a limiting sense, because numerous variations are possible. The specific routines or methods described herein may represent one or more of any number of processing strategies.

The foregoing devices and operations, including their implementation, will be familiar to, and understood by, those having ordinary skill in the art. This specification contains numerous dimensions, all of which could be changed without deviating from the inventions herein.

The above description of the embodiments, alternative embodiments, and specific examples, are given by way of illustration and should not be viewed as limiting. Further, many changes and modifications within the scope of the present embodiments may be made without departing from the spirit thereof, and the present inventions include such changes and modifications.

LISTING OF DRAWING ELEMENTS

100 eye
102 anterior chamber
104 conjunctiva
106 episcleral vein
108 aqueous vein
110 iris
112 Schlemm's canal
114 trabecular meshwork
116 lens
118 sclera
120 ciliary body
122 collector channels
124 aqueous humor
126 cornea
128 zonules
202 implant
204 perforations
206 proximal tip
208 distal end
210 lumen
302 pupil
304 scleral flap
402 Goniotomy
404 clear corneal incision
502 electrodes
602 pressure sensor
604 controller
606 power source
704 ports
802 regulator
804 recharging circuit
806 antenna
808 power rail
900 electrolysis method
902 block
904 block
906 block
908 block
910 block
912 block
914 block

What is claimed is:

1. An apparatus comprising:
   an ocular implant with a curved longitudinal central axis with a bend in a curvature plane, the ocular implant including a central channel and an array of perforations along walls of the ocular implant, the ocular implant configured to be disposed within Schlemm's canal of an eye;
   a pair of electrodes lining an inside of the walls of the ocular implant;
   a controller within the ocular implant electrically connected to the pair of the electrodes; and
   a power source within the ocular implant electrically connected to the controller.

2. The apparatus of claim 1 wherein the power source delivers electrical current to the electrodes.

3. The apparatus of claim 1 wherein the electrodes are arranged in a coil within the ocular implant.

4. The apparatus of claim 1 further comprising a pressure sensor electrically connecting to the controller, the pressure sensor configured to detect pressure within the ocular implant.

5. The apparatus of claim 1 further comprising an antenna electrically connected to the controller, said antenna configured to wirelessly communicate with a remote receiver.

6. The apparatus of claim 1 where the electrodes are made of titanium.

7. The apparatus of claim 1 where the ocular implant is made of polyurethane.

8. The apparatus of claim 1 further comprising a lumen at an end of the ocular implant, the lumen configured to receive aqueous humor from the eye.

9. A method comprising:
performing a fornix-based conjunctival peritomy;
creating a scleral flap beneath a conjunctiva in a region of the fornix-based conjunctival peritomy;
exposing Schlemm's canal;
inserting a proximal end of a ocular implant into an incision into the Schlemm's canal, where the ocular implant includes a central channel and an array of perforations along walls of the ocular implant, a pair of electrodes lining an inside of the walls of the ocular implant, a controller within the ocular implant electrically connected to the pair of the electrodes, and a power source within the ocular implant electrically connected to the controller;
suturing the scleral flap; and
performing electrolysis by energizing the electrodes with a signal from the controller.

10. The method of claim 9 where the signal from the controller is a current that is delivered by the power source to the electrodes.

11. The method of claim 9 where the controller uses the signal to perform the electrolysis by regulating a level of current, a duration of the current, and a timing of the current.

12. The method of claim 9 where the perforations in the walls allow ingress of aqueous humor into the central channel of the ocular implant.

13. The method of claim 9 where the perforations in the walls allow egress of gas from the central channel of the ocular implant.

14. The method of claim 9 where the electrodes are made of platinum.

15. The method of claim 9 where the electrodes are made of graphite.

16. A method comprising:
receiving a signal from a remote device at a controller in an ocular implant, where the ocular implant is located in Schlemm's canal of an eye, where the ocular implant includes a central channel and an array of perforations along walls of the ocular implant, a pair of electrodes lining an inside of the walls of the ocular implant, the controller electrically connected to the pair of the electrodes, a pressure sensor electrically connecting to the controller, and a power source within the ocular implant electrically connected to the controller;
detecting a pressure within the ocular implant with the pressure sensor;
analyzing the pressure with the controller and determining if electrolysis is required to reduce the pressure;
energizing the electrodes by asserting power on a signal from the controller;
monitoring the pressure with the pressure sensor until the pressure indicates that the electrolysis is no longer required; and
de-energizing the electrodes by de-asserting power on the signal from the controller.

17. The method of claim 16 where the signal from the controller triggers a relay to deliver current from the power source to the electrodes.

18. The method of claim 16 where the perforations in the walls allow ingress of aqueous humor into the central channel of the ocular implant.

19. The method of claim 16 where the perforations in the walls allow egress of gas from the central channel of the ocular implant.

20. The method of claim 16 where the ocular implant is made of silicone.

\* \* \* \* \*